(12) United States Patent
Oehme et al.

(10) Patent No.: US 8,935,431 B2
(45) Date of Patent: Jan. 13, 2015

(54) HIGHLY SCALABLE AND DISTRIBUTED DATA SHARING AND STORAGE

(75) Inventors: Sven Oehme, San Jose, CA (US); Marc Thadeus Roskow, Los Gatos, CA (US); Stephen Leonard Schwartz, Tucson, AZ (US); Anna W. Topol, Jefferson Valley, NY (US); Daniel James Winarski, Tucson, AZ (US)

(73) Assignee: International Business Machines Corporation, Armonk, NY (US)

( * ) Notice: Subject to any disclaimer, the term of this patent is extended or adjusted under 35 U.S.C. 154(b) by 801 days.

(21) Appl. No.: 12/971,129

(22) Filed: Dec. 17, 2010

(65) Prior Publication Data

US 2012/0158882 A1 Jun. 21, 2012

(51) Int. Cl.
*G06F 19/00* (2011.01)
*G06F 17/30* (2006.01)

(52) U.S. Cl.
CPC ........ *G06F 17/30224* (2013.01); *G06F 19/321* (2013.01)
USPC ........... 709/248; 709/246; 709/238; 709/223; 709/208

(58) Field of Classification Search
CPC ............................... G06F 19/321; G06F 19/00
USPC .............. 709/226, 217, 221, 213, 225; 705/3; 382/239; 717/178; 707/737; 714/47.1; 435/189, 43, 6.1, 69.1
See application file for complete search history.

(56) References Cited

U.S. PATENT DOCUMENTS

| | | | |
|---|---|---|---|
| 7,284,017 B2 * | 10/2007 | Baune | 707/823 |
| 7,640,171 B2 | 12/2009 | Gendron et al. | |
| 2004/0205148 A1 * | 10/2004 | Bae et al. | 709/213 |
| 2005/0289414 A1 * | 12/2005 | Adya et al. | 714/724 |
| 2007/0206676 A1 * | 9/2007 | Yamazaki | 375/240.12 |
| 2008/0021740 A1 * | 1/2008 | Beane et al. | 705/3 |
| 2010/0123732 A1 | 5/2010 | Jenks et al. | |

OTHER PUBLICATIONS

Michael Adam, Clustered NAS for Everyone, Clustering Samba With CTDB, Samba Team/SerNet GmbH, http://www.samba.org/~obnox/presentations/nluug-spring-2009/nluug-spring-2009-paper-obnox.pdf.*

* cited by examiner

*Primary Examiner* — David Lazaro
*Assistant Examiner* — Charles Murphy
(74) *Attorney, Agent, or Firm* — Zilka-Kotab, PC

(57) ABSTRACT

Embodiments of the disclosure relate to storing and sharing data in a scalable distributed storing system using parallel file systems. An exemplary embodiment may comprise a network, a storage node coupled to the network for storing data, a plurality of application nodes in device and system modalities coupled to the network, and a parallel file structure disposed across the storage node and the application nodes to allow data storage, access and sharing through the parallel file structure. Other embodiments may comprise interface nodes for accessing data through various file access protocols, a storage management node for managing and archiving data, and a system management node for managing nodes in the system.

3 Claims, 6 Drawing Sheets

HIGHLY SCALABLE AND DISTRIBUTED DATA SHARING AND STORAGE

BACKGROUND

The disclosure relates generally to computer data storage, and more particularly to highly scalable and distributed data sharing and storage using parallel file systems.

Systems and applications in specialized fields, like those in healthcare, are increasingly interconnected by networks, generating large amounts of data, and sharing data produced by interconnected devices. For example, in a hospital environment, computed axial tomography (CAT) and magnetic resonance imaging (MRI) systems may be producing MRI and CAT images for some patients while bio-assay instruments in the hospital's laboratories may be recording test results for other patients. At the same time, doctors and nurses may be generating, accessing, and storing patient data from numerous interconnected medical equipment, devices, and workstations in the hospital. The data may be in different file system formats. It is often a challenge to provide an efficient and readily scalable mechanism for storing and accessing data in such a widely distributed, interconnected, and diverse system.

In a typical large networked environment, various specialized equipment, devices, client and server computers may send their data through a network to a centralized data storage system for storing. The data storage system may maintain data in a particular file structure. When data is later accessed by application modalities in the network, the data is retrieved and may need to be transformed to other file system formats before the accessing modalities may use it. Such a process causes delays due to the conversion from one file format to another. In addition, when archiving data, excessive delays may be encountered in a data storage system which does not scale well and requires several independent storage subsystems within the network. The application modalities would need to search for desired data in such independent subsystems.

As the number of interconnected modalities in various computers, devices and equipment increases, more data is generated and shared among these application modalities. In addition, the application modalities may be in different types of devices and systems, produced by various manufacturers, and may use different file protocols for storing and sharing data.

Other environments that have a large number of interconnected application modalities and substantial amount of shared data include oil and mineral exploration, retail, stock trading, weather forecast, space exploration, seismic data collection, military intelligence, security and surveillance, digital motion pictures, etc.

There is such as a need for a highly scalable distributed system that enables seamless storing and sharing of a large volume of data among a large number of interconnected devices, systems, and applications.

BRIEF SUMMARY OF THE DISCLOSURE

The disclosure relates to highly scalable system, method and computer program product for storing and sharing data among interconnected application modalities in a distributed environment using a parallel file system. One aspect of the disclosure concerns a system that may comprise at least one storage node coupled to a network for storing data, one or more application nodes coupled to the network, and a parallel file structure. The parallel file structure may be implemented across the storage node and application nodes to allow data storage, access and sharing among the nodes through the parallel file structure. The application nodes may be interconnected modalities that are part of devices, systems, and computers in a large networked environment.

In one embodiment of the invention, the distributed system may comprise one or more interface nodes to allow users to access files and interact with modalities in the system through the parallel file structure. The distributed system may further comprise a storage management server for managing and archiving data in the system and a system management node for managing the operation of the application nodes, interface nodes, storage nodes, and storage management server.

Another aspect of the disclosure concerns a computer implemented method for storing and sharing data in a highly scalable and distributed environment through a parallel file structure. Still another aspect of the disclosure concerns a computer program product for storing and sharing data in a highly scalable and distributed environment through a parallel file structure.

The details of the embodiments of the disclosure, both as to their structure and operation, are described below in the Detailed Description section in reference to the accompanying drawings. The Brief Summary is intended to identify key features of the claimed subject matter, but it is not intended to be used to limit the scope of the claimed subject matter.

DETAILED DESCRIPTION OF THE DISCLOSURE

Figure 1:
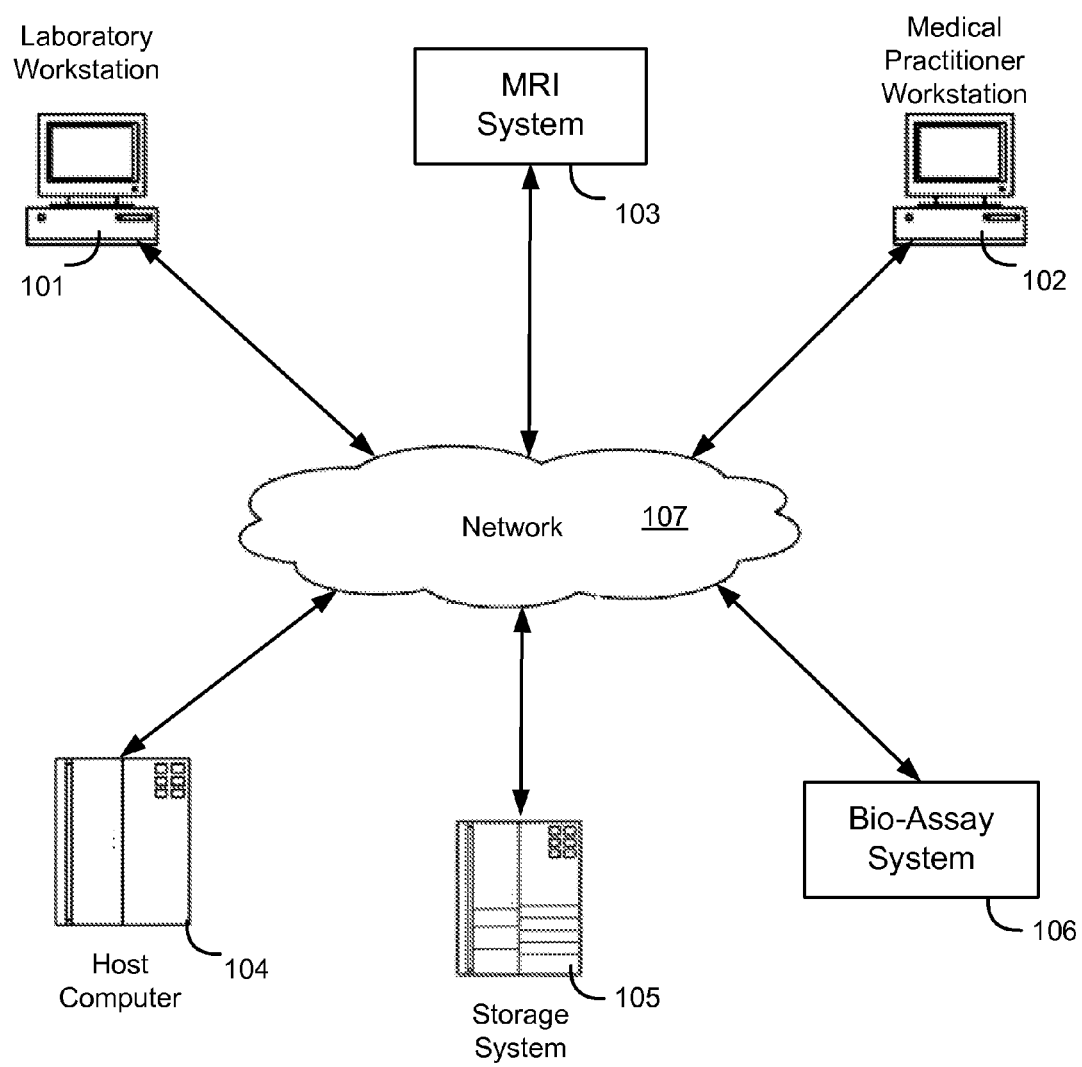
FIG. 1 illustrates an exemplary configuration of interconnected and distributed computing and storage systems in which aspects of the disclosure may be provided.

Embodiments of the disclosure relate to data storing and sharing in a scalable and distributed computing environment to allow efficient data access among a large number of networked application modalities based on parallel file systems and file access protocols. The application modalities may be part of specialized instruments, devices, systems, and applications that are widely distributed and interconnected by networks in an enterprise. The embodiments further relate to managing, archiving and retrieving of the data in such a highly scalable and distributed environment. The high-density high-performance architecture of the embodiments virtualizes and consolidates file formats into an enterprise-wide file system which translates into reduced cost and enhanced operational efficiency.

Storage systems which optimize the concept of file sharing across the network are often referred to as network attached storage (NAS) systems. NAS systems may use the mature Ethernet IP network technology of the LAN. Data may be sent to and from NAS devices over the LAN using TCP/IP protocol. One of the key differences in a NAS appliance, compared to direct attached storage or other network storage solutions such as SAN or iSCSI, is that all client I/O operations to the NAS use file level I/O protocols. File I/O is a high level type of request that, in essence, specifies only the file to be accessed, but does not directly address the storage device. This is done later by other operating system functions in the remote NAS appliance.

By making storage systems LAN addressable, the storage is freed from its direct attachment to a specific server, and any-to-any connectivity is facilitated using the LAN fabric. In principle, any user running any operating system can access files on the remote storage device. This is done by means of a common network access protocol—for example, NFS for UNIX® servers and CIFS for Windows servers. In addition, a task such as backup to tape can be performed across the LAN using software like Tivoli Storage Manager™ (TSM), enabling sharing of expensive hardware resources (for example, automated tape libraries) between multiple servers.

NAS file system access and administration network access methods like NFS and CIFS can only handle file I/O requests to the remote file system. This is located in the operating system of the NAS device. I/O requests are packaged by the initiator into TCP/IP protocols to move across the IP network. The remote NAS file system converts the request to block I/O and reads or writes the data to the NAS disk storage. To return data to the requesting client application, the NAS appliance software repackages the data in TCP/IP protocols to move it back across the network.

In order to use a storage device attached to a LAN, the system may need to provide certain utilities to manage the transfer and the organization of data on the device. These utilities may be provided by a dedicated server to which the common storage is attached. A NAS system typically comprises a server, an operating system, and storage which is shared across the network by many other servers and clients. Today's NAS file systems, however, do not scale to high capacities. When one filer was fully utilized, a second, third, and more filers were installed. As a result, system administrators may need to managing many filers. Capacity on individual filers could not be shared. Some filers were heavily accessed while others were mostly idle.

Managing the many different filers adds further complexity to the administrator's job. When adding more storage capacity to some filers; one cannot add more performance to a particular file, than what is possible with the single disk drive or controller that the filer typically uses. In other words, there is limited parallelism, (typically, one, two, or a few controllers) for serving an individual file. The embodiments of the invention provide a distributed storage architecture that is highly scalable based on a parallel file system implemented across the distributed nodes.

Referring to the drawings and in particular to FIG. 1, there is illustrated an example configuration of interconnected and distributed computing in which aspects of the invention may be provided. The configuration in FIG. 1 is presented only by way of example and is not intended to be limiting. The scalable and distributed data storage systems and methods disclosed herein may be applicable to a wide variety of different computers, servers, storage systems, and networks. The illustrated configuration may comprise one or more host computers 104 that communicate with other workstations, such as laboratory workstation 101 and medical practitioner workstation 102, as well as specialized systems, such as MRI system 103 and bio-assay system 106, through computer network 107. A medical practitioner may include a doctor, nurse, lab technician, dentist, etc. The computer network 107 may comprise one or more wide area networks (WANs), local area network (LANs), private intranets and the Internet.

Host computers 104 may include CPUs (Central Processing Units) and memory for executing various programs, thereby providing a variety of computing functions to workstations 101-102 and systems 103, 106 in the networked configuration. For example, the host computer 104 may be a server that hosts applications for providing computing services such as web services and database applications. The distributed configuration 100 may be part of a large customer operation or enterprise such as a major medical facility. As such, there may be specialized equipment and devices serving various operations in the medical facility that are also connected to the network 107, such as an magnetic resonance imaging (MRI) system 103 and an bio-assay system 106.

The distributed configuration 100 may further include one or more storage system 105 for storing data. Multiple storage systems 105 may be interconnected through a network (not shown) such as a storage area network (SAN), a LAN (Local Area Network), a Fibre Channel interface or other host interface protocols. A SAN is a dedicated high performance network between servers and storage resources, such as Fibre Channel (FC), Enterprise Systems Connection (ESCON), Small Computer Systems Interface (SCSI), Internet SCSI (iSCSI), Serial Storage Architecture (SSA), High Performance Parallel Interface (HIPPI), or other protocols with similar functions. A data storage system 105 may comprise hard disk drives, solid state drives, arrays of hard disk drives or solid-state drives, tape drives, tape libraries, CD-ROM libraries, or the like. Further, the data storage system 105 may comprise multiple levels such as a primary level of solid state storage, a secondary level of disk storage, and a third level of tape libraries.

A storage system 105 may comprise one or more storage controllers, disk arrays and tape libraries. For example, the storage system 105 may comprise IBM TotalStorage™ systems DS8000®. The DS8000® systems are high-performance, high-capacity storage controllers providing disk storage that is designed to support continuous operations. The storage controllers may include host adapters for interfacing with host computer 104 and device adapters for interfacing with attached storage devices such as disks and solid state drives. The host adapters may support various host-device interface protocols such as Fibre Channel (FC), Fibre Channel Arbitration Loop (FC-AL), Internet Small Computer System Interface (iSCSI), etc.

Users and computer programs may store data on storage system 105 and retrieve data from them, using various data processing applications and storage management software running in the host 104 and the storage system 105. The storage management software may provide, among other functions, utilities for managing data in the storage system 105 such as data backup, restore, copy, recovery, migration, and archiving. In another embodiment, storage system 105 may be an IBM System Storage™ TS7650 ProtecTIER® Deduplication Appliance. In yet another embodiment, storage system 105 may be an IBM System Storage™ TS3500® tape library system.

Figure 2:
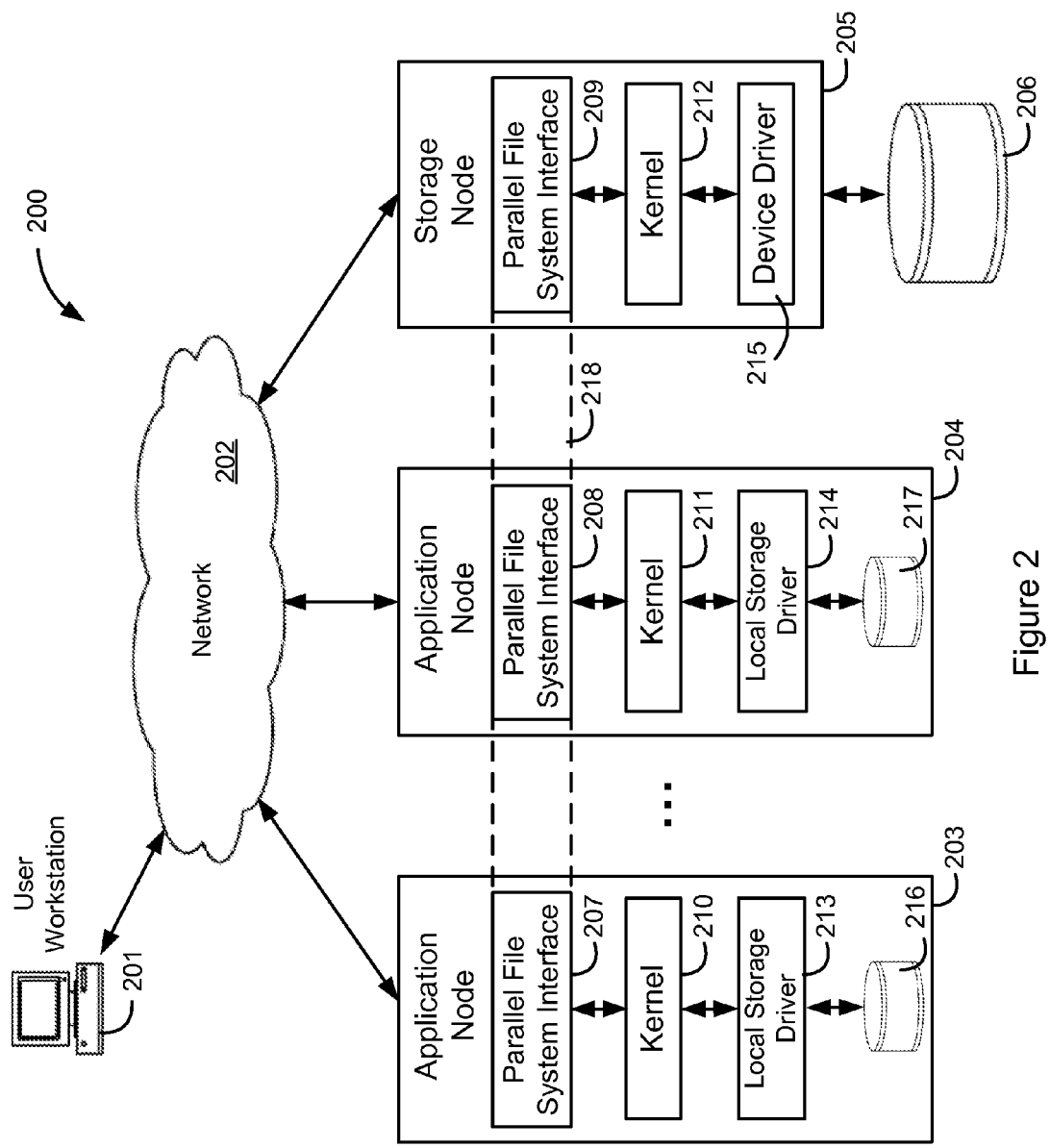
FIG. 2 illustrates a block diagram of a distributed data sharing and storage system that includes multiple application nodes and a storage node, according to an exemplary embodiment of the disclosure.

FIG. 2 illustrates a block diagram of a scalable distributed data sharing and storage system 200 according to an exemplary embodiment of the disclosure. As an example, the distributed system 200 may be a network of multiple client workstations, servers, data storage, and computer-based medical systems, devices, and equipment in a large hospital or medical facility, but is not limited to such an environment. The workstations, as represented by workstation 201, may include portable devices used by doctors for reviewing existing patient data and entering new data when examining the patients, and those used by medical staff at various workstations in the hospital, such as laboratory workstation 101 and medical practitioner workstation 102. The workstation 201 may communicate with other computers, devices, systems, and medical equipment in the hospital through a network 202. The network 202 may be wired, wireless, or a combination thereof, and may be based on a network protocol such as Ethernet, Gigabit Ethernet, Fibre Channel over Ethernet, iSCSI, and the like.

In one embodiment, the distributed system 200 may comprise a large number of application nodes 203-204 for providing aspects of the invention. An application node 203-204 may be implemented in a client computer, a server, or a specialized device, system, or equipment with appropriate computing and network support. As examples, the application nodes 203-204 may be provided in the medical staffs workstations, MRI and CAT machines, biological analysis and assaying systems, server computers, etc., all of which may be connected to the hospital's network infrastructure 202. The application nodes 203-204 are referred to as application modalities.

The application nodes 203-204 may comprise parallel file system interfaces 207-208 to allow the application nodes 203-204 to communicate with each other, and with other components in the distributed system 200 at file level through a parallel file system 218. An application running in application nodes 203-204 may communicate with other nodes and components in the system 200 through the parallel file system 218 by making system calls to kernels 210-211 which are respectively coupled to parallel file system interfaces 207-208.

The parallel file system 218, also referred to as a distributed file system or network file system, is a file system that allows access and sharing of files from multiple computers in a network. Significant advantages of a parallel file system are its scalability and high performance as more computer nodes may be added to the network as the system expands in size, but the file system continues to provide similar functions and performance. In one embodiment of the invention, the parallel file system 218 may be an IBM General Parallel File System™ (GPFS), but other parallel file systems may be used such as the Andrew File System (AFS), Network File System (NFS), Server Message Block (SMB), Global File System (GFS), and Cluster File System (CFS). Details on the General Parallel File System (GPFS) are described below with reference to FIG. 3.

Application nodes 203-204 may respectively comprise local storage devices 216-217 such as disk drives, solid state drives or optical disk drives for holding local and temporary data. For example, an MRI system or a biological testing equipment may include local disk drives for storing patient images and test results data collected during peak operation hours, which are then transmitted to the hospital's main data storage systems during off-peak hours. Applications running in application nodes 203-204 and other devices and systems in the distributed network may access data stored on local storage devices 216-217 of the respective application nodes 203-204 through local storage device drivers 213-214. Device drivers 213-214 may reside within kernels 210-211 or be in direct communication with kernels 210-211.

The distributed system 200 may further comprise a storage node 205 for storing large amounts of data generated by various nodes and components in the distributed system and for sharing data among the nodes and components in the system. The storage node 205 may comprise a parallel file system interface 209 for communicating with other nodes, such as application nodes 203-204, and components of the distributed system 200 through the parallel file system 218. Applications running in the storage node 205 may interface with the parallel file system 218 by making system calls to a kernel 212 coupled to the parallel file system component 209. In a large operation, the storage node 205 may be part of a data storage system 105 which may comprise multiple data storage controllers attached to multiple data storage devices 206. For example, the storage node 205 may operate in an IBM DS8000® storage system that includes multiple RAID disk arrays 206 which are accessed via device driver 215. Device driver 215 may reside within kernel 212 or be in direct communication with kernel 212.

Figure 3:
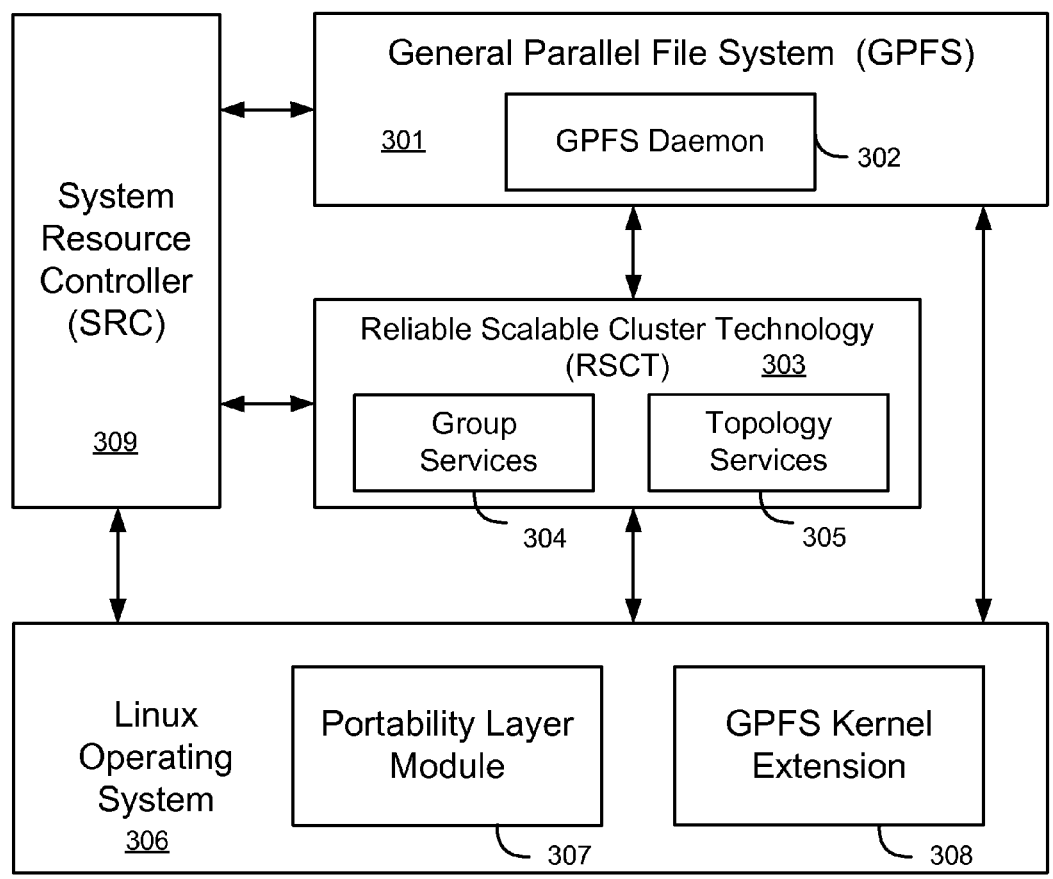
FIG. 3 illustrates a block diagram of an IBM General Parallel File System™ (GPFS), according to an embodiment of the disclosure.

FIG. 3 illustrates key components of an IBM General Parallel File System™ (GPFS) implementation. GPFS is a parallel and shared disk file system. The parallel nature of GPFS guarantees that the entire file system is available to all nodes within a defined scope and the file system's services can be safely applied to the same file system on multiple nodes simultaneously. GPFS allows shared access to files that may span multiple disk drives on multiple nodes. It offers many of the standard UNIX® file system interfaces, allowing most applications to execute without modification or recompiling. UNIX® file system utilities are also supported by GPFS. That is, users can continue to use the UNIX® commands they have always used for ordinary file operations. The only new commands are those for administering the GPFS file system.

GPFS allows parallel applications simultaneously access to the same files, or different files, from any node while managing a high level of control over all file system operations. A typical GPFS implementation may include a GPFS daemon 302 in a GPFS layer 301, a reliable scalable cluster technology (RSCT) layer 303, a Linux operating system 306, and a system resource controller 309. The RSCT layer 303 may include a group services daemon 304 and a topology services daemon 305. The Linux operating system 306 may include a portability layer module 307 and a kernel extension 308.

The kernel extension 308 provides interface to a virtual file system (VFS) for accessing a file system. GPFS daemon 302 is a multi-threaded process with some threads dedicated to specific functions. This ensures that services requiring priority attention are not blocked because other threads are busy with routine work. The GPFS daemon 302 also communicates with instances of the daemon 302 on other nodes in the distributed system to coordinate configuration changes, recovery, and parallel updates of the same data structures.

The GPFS daemon 302 may reside in general parallel file system 301 and include the following functions:
Allocation of disk space to new files and newly extended files.
Management of directories, including creation of new directories, insertion, removal of entries into existing directories, and searching of directories that require I/O.
Allocation of appropriate locks to protect the integrity of data and metadata.

Locks affecting data that may be accessed from multiple nodes require interaction with the token management function.

Disk I/O is initiated on threads of the daemon.

Security and quotas are also managed by the daemon in conjunction with the File System Manager.

A typical GPFS implementation may further include Reliable Scalable Cluster Technology (RSCT) daemons 304-305 in a RSCT layer 303 to provide topology and group services, i.e., the illustrated "hagsd" and "hatsd" daemons. The hagsd daemon 304 may relate to a group service subsystem which provides other subsystems with a distributed coordination, messaging, and synchronization. The hatsd daemon 305 may relate to the topology service subsystem which provides other subsystems with network adapter status, node connectivity information, and a reliable messaging service. To enable communication between the Linux kernel and the GPFS kernel extension modules 308, GPFS may further provide a portability module 307 that is based on the particular hardware platform and Linux version. The portability module 307 and GPFS kernel extension 308 may operate in the Linux operating system 306. A system resource controller (SRC) 309 provides commands and subroutines for creating and control programs in a cluster environment. The SRC 309 may include functions for program start and stop, status inquiry, trace, and control of a remote system.

Figure 4:
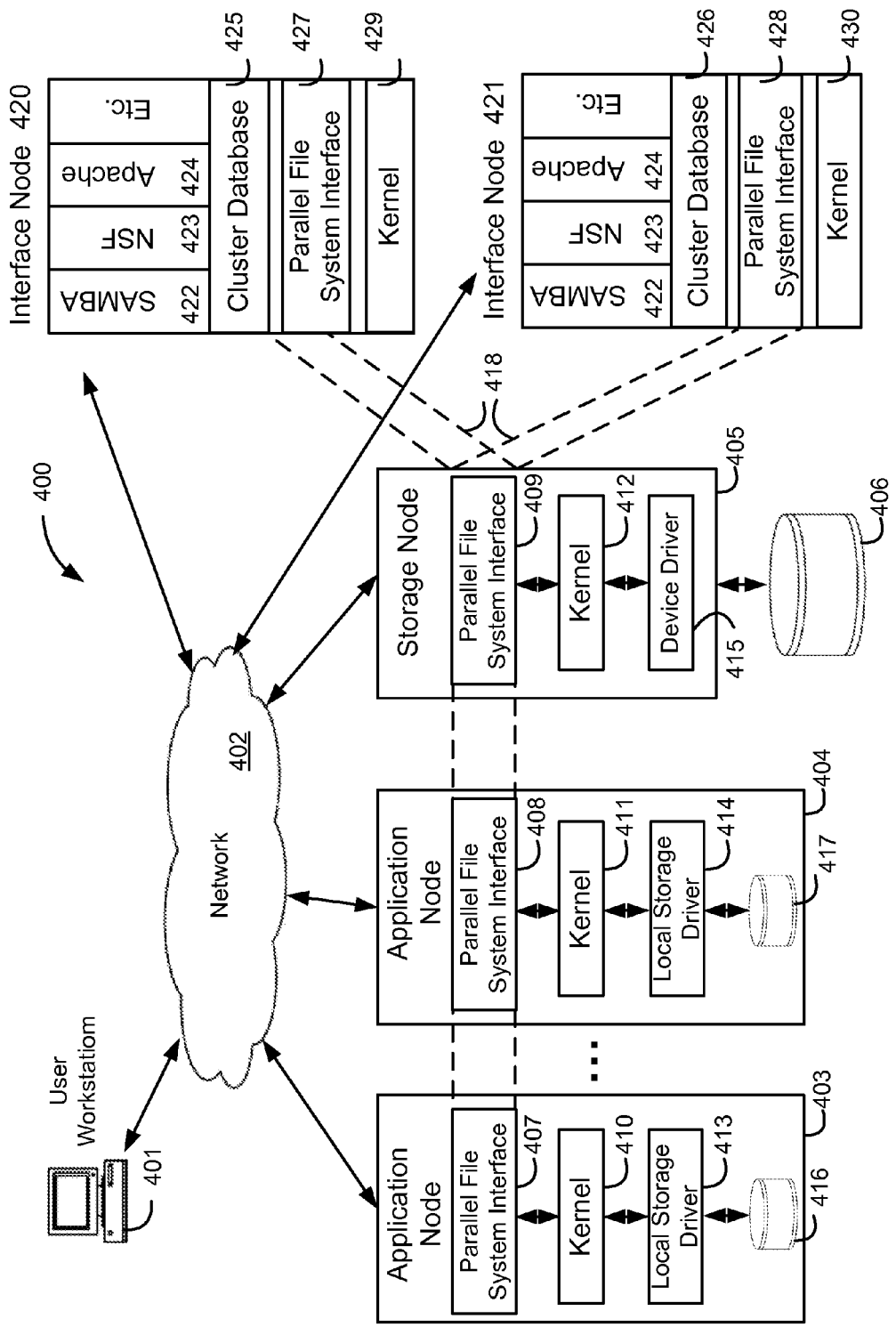
FIG. 4 illustrates a block diagram of a distributed data sharing and storage system that includes an application node, a storage node, and multiple interface nodes, according to an exemplary embodiment of the disclosure.

FIG. 4 illustrates a block diagram of a second exemplary embodiment of a scalable and distributed data sharing and storage system 400. In addition to application nodes 403-404 and storage node 405 described with reference to FIG. 2 above, the distributed storage system 400 may include one or more interface nodes 420-421 to allow users to interact with the application nodes 403-404 and access data generated and stored in the distributed system 400. One or more interface nodes 420-421 and storage nodes 405 may share equally in the distributed system 400 to balance workloads dynamically and provide parallel performance to all users and storage, while assuring high availability and automated failover. The distributed system 400 achieves dynamic load-balancing as all nodes share equally in the reading and writing of files in parallel from all disk in the system, through the parallel file system 418.

Interface nodes 420-421 may be implemented in user workstations or devices having access to the network that interconnects the application modalities, such as Ethernet, Gigabit Ethernet, iSCSI, Fibre Channel over Ethernet, Fibre Channel, etc. Each interface node 420-421 may include one or more file access modules 422-424 for accessing the parallel file system 418 using respective file access protocols that the file access modules 420-421 support. The supported file access protocols may include, for example, SAMBA, Common Internet File System (CIFS), Network file System (NFS), Apache, Hypertext Transfer Protocol Secure (HTTPS), Very Secure File Transfer Daemon (VSFTD), File Transfer Protocol (FTC), and Secure Socket Shell Daemon (SSHD).

The Samba protocol provides file access services around the CIFS protocol and integration for a Microsoft Windows™ environment. Windows™ clients thus can access share files defined in Samba with the same procedures for accessing share files on a native Windows™ server. SMB client utilities may be provided for UNIX® systems and since Windows™ clients already support NetBIOS over TCP/IP, they do not require additional software beyond allowing NetBIOS access.

When sharing files via NFS between Windows™ and UNIX® systems, or other disparate systems, both ends of the transaction must run NFS software. One end must run the server daemons, and the other must run the client daemons. In a Windows™ environment, the services provided by the share file system would appear as Windows™ file services. A typical implementation of Samba may provide the following functions: full CIFS data access and transfer capabilities, user authentication, file access control lists on files and directories, and failover. Further information on Samba is available at http://www.samba.org. The Apache daemon provides HTTPS access to the file system. The file system may encrypt user credentials to provide secure access to files in the system.

In order to support a large number of files shared by nodes in the distributed system 400, the interface nodes 420-421 may respectively include cluster database components 425-426 for interfacing with file access modules 422-424, and parallel file system interfaces 427-428 to parallel file system 418. As in the application nodes 403-404 and storage node 405, applications running in the interface nodes 420-421 may communicate with the parallel file system interfaces 427-428 by making system calls to kernels 429-430, which may be coupled to parallel file system interfaces 427-428, respectively.

In one embodiment, the database components 425-426 may comprise a cluster trivial database (CTDB) implementation. CTDB is an open source software for providing clustered CIFS, clustered NFS and other clustered network file protocols on top of SAMBA and a clustered file system. CTDB ensures consistent data and file locking across all nodes in a cluster, and provides high availability (HA) features, such as node monitoring, node fail-over and IP address take over. CTDB has two major responsibilities. First, it provides a clustered implementation of Samba's trivial database and distributes record updates across the cluster. Individual nodes take ownership of individual records and only the owning node has the most recent copy of the record. Nodes also take the ownership to update the record. This design provides high scalability.

The second responsibility of CTDB is the control of the cluster. In a two-layer architecture with storage and a network attached storage (NAS) layer, a cluster in terms of CTDB means the nodes of the NAS layer. CTDB controls the public IP addresses used to publish the NAS services and moves them between nodes. Through monitoring scripts, CTDB may determine the operational state of a node. If a node has problems, like broken services, network links, etc., the node becomes inoperable. In this case, CTDB migrates all public IP addresses to operating nodes and sends so-called tickle-acks to the clients so that they could reestablish the connection. CTDB may further provide the following capabilities:

Functions to provide consistent data and consistent locking across all nodes in a cluster;

Functions to automatically recover and repair all TDB databases that CTDB manages in case of node failures;

Support for parallel CIFS (pCIFS) with Samba;

Reliable messaging transport to allow applications linked with CTDB to communicate to other instances of the application running on different nodes in the cluster;

Pluggable transport backends such as TCP and Infiniband; and

Support for application specific management scripts to allow applications that depend on network or file system resources to be managed in a highly available manner on a cluster.

In one embodiment, the communications between network 402 and application nodes 403, 404 and storage node 405 may occur through interface nodes 420 and 421. In another embodiment, initial and final communications between network 402 and application nodes 403, 404 and storage node 405 may occur through interface nodes 420 and 421 as the CTDB 425, 426 handles the locking and unlocking of files; however, for performance reasons, all communications other than the initial and final communications may occur directly between the network 402 and application nodes 403, 404 and storage node 405. The application nodes 403-404, storage node 405, interface nodes 420-421, and network 402 were described in detail above with reference to FIG. 2.

Figure 5:
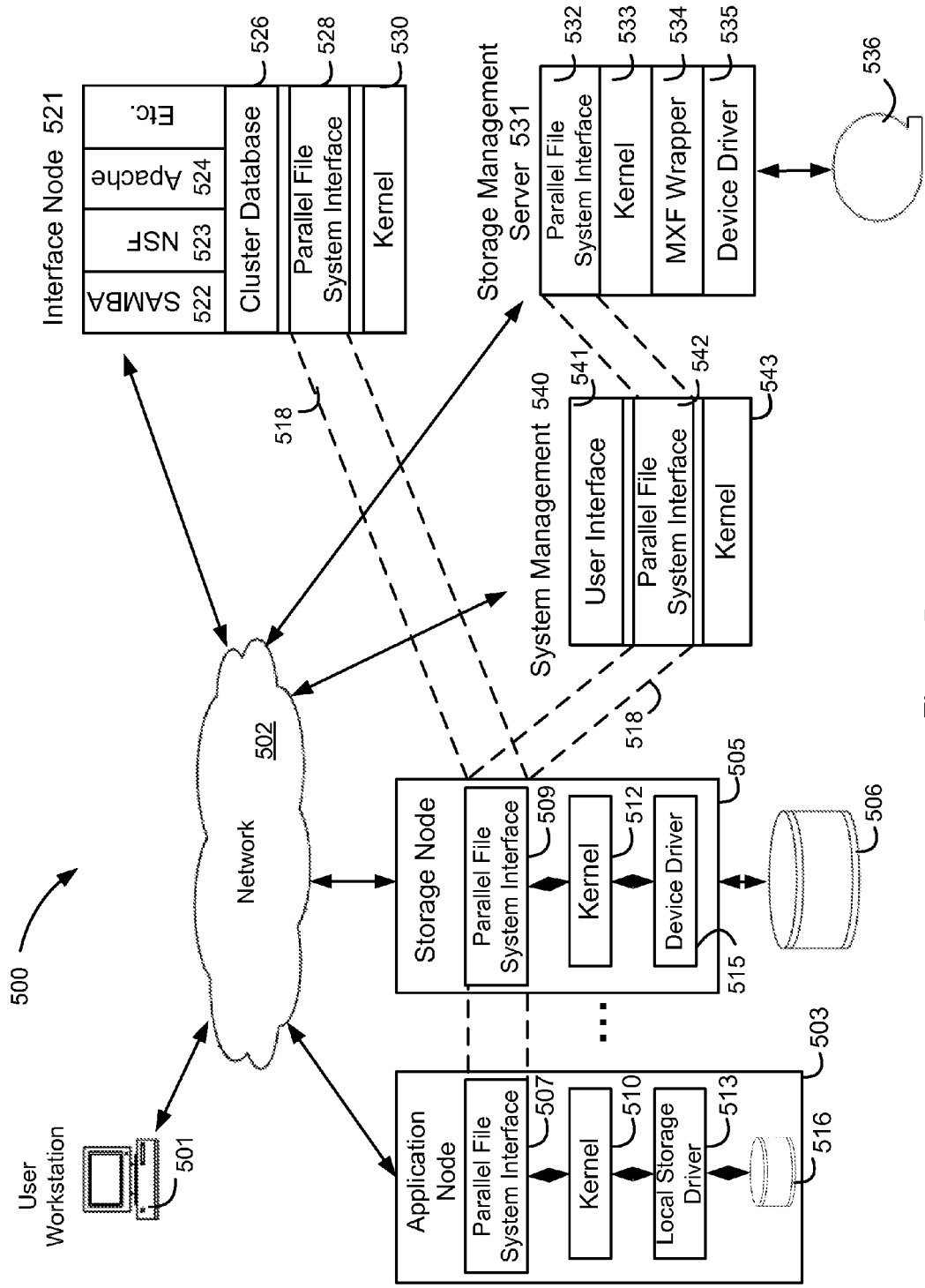
FIG. 5 illustrates a block diagram of a distributed data sharing and storage system that includes an application node, a storage node, an interface node, a storage management server, and a system management node, according to an exemplary embodiment of the disclosure.

FIG. 5 illustrates a third exemplary embodiment of a scalable distributed data sharing and storage system 500. In addition to one or more application nodes 503, storage nodes 505, and interface nodes 521 as described with reference to FIGS. 2 and 4, the distributed system 500 may include a storage management server 531. The storage management server 531 facilitates the management, backup, restore, and archiving of large amounts of data in the distributed system 500 through the parallel file system 518. As an example, the storage management server 531 may comprise an IBM Tivoli Storage Manager™ (TSM).

The Tivoli Storage Manager™ provides accelerated backup and restore capability with high performance, using a connection such as NFS or CIFS. In addition, the Tivoli Storage Manager™ provides hierarchical storage management (HSM) of data in the distributed system to external tape, tape libraries, virtual tape libraries, or de-duplication devices. In the illustrated embodiment, the storage management server 531 may include a parallel file system interface 532 for communicating at the file level with other nodes and components in the distributed system 500. Applications in the storage management server 531 may interface with the parallel file system interface 532 by making system calls to a kernel 533 coupled to the parallel file system interface 532.

In one embodiment, the Tivoli Storage Manager™ backup and archive client code may run on one or more interface nodes under the control of a command line interface (CLI) of the distributed system. The CLI allows the specification of client parameters such as the address of the TSM server for an include-exclude list. Use of the TSM copy within the system may be specifically targeted at full file system incremental backups using a backup accelerator. A user may tailor the backup by the specification of TSM options through the command line including include/exclude statements. The performance gains from using a backup accelerator make this an optimal way to backup data in the distributed system.

In another embodiment, the TSM client may run on an external server and support data backup over NFS and CIFS. Such an embodiment may be more suitable for backing up files associated with a specific user because the TSM client runs with the user's credentials, rather than requiring administrative authority. A TSM space management client may optionally run on an interface node 521 for the purpose of allowing migration of files from on-line storage to near-line storage. The command line interface may support a managed file system which links the GPFS code for the file system to an instance of TSM which will migrate files to a named TSM server. The command line interface may allow the specification of the interface node 521 to run the migration processes. The migration may provide one instance of the migration processes per file system with a failover node. Mount of the file system is dependent on this migration process being active and connected to a server.

The storage management server 531 may be attached to one or more tape library 536 for archiving data in the distributed system 500 to the library 536. As an example, the tape library 536 may comprise IBM TS1130™ enterprise tape drives or Linear Tape Open (LTO) tape drives. The storage management server 531 may communicate with the tape library 536 through device driver 535. Device driver 535 may reside within kernel 533 or be in direct communication with kernel 533. A device driver is a computer program allowing higher level computer programs to interact with a hardware device. In Linux environments, programmers can build device drivers either as parts of the kernel or separately as loadable modules. A data archiving typically moves data from one storage tier (e.g., disks) to a lower storage tier (e.g., tapes) in a data storage hierarchy. The storage tier holding the archived data generally has a slower response time, lower cost per data unit, and larger capacity than the tier from which data is archived. Data is generally archived in units of volumes and the archival may be to a local or a remote storage system.

The storage management server 531 may optionally include a Material Exchange Format (MXF) wrapper 534 for encapsulating images and video, such as medical images generated by MRI and CAT equipment in a hospital, for archiving purposes. MXF metadata and thumbnail images could be stored in one partition of the LTO-5 tape cartridge, while the fully detailed medical images and video could be stored in the other partition of the LTO-5 tape cartridge. A user at user computer 501 could view thumbnail images before deciding what medical images and video to upload from the tape library 536. Medical images could be bundled as a series of I-frames in a video stream, for the purpose of using MXF data.

The storage management server 531 may provide functions for policy based management of data and tiered storage management in the system 500, through a parallel file system interface 532. The parallel file system 518, such as GPFS, may provide physical file system capabilities for the distributed system 500 by allowing the mount of a collection of GPFS file systems 518 on a set of interface nodes 521 for service to client machines external to the system 500. GPFS may accept as input a collection of storage logical units (LUNs) connected through the storage nodes 505 and application nodes 503, and make them into a file system. This file system can then be accessed by applications running on a series of nodes. The applications may be file serving programs which provide file services to external clients. GPFS provides full POSIX semantics and some extensions for Windows™ export via Samba.

The distributed system 500 may further include a system management node 540 for managing the operation of the application node 503, interface node 521, storage node 505, and storage management server 531. The system management node 540 is connected to network 502 and may comprise a parallel file system interface 542 for communicating with other nodes and components in the distributed system 500, at the file level, through the parallel file system 518. Inter-node communication, which is the direct communication between the application node 503, storage node 505, interface node 521, management nodes 531 and 540, and the like, may be accomplished through a backbone, using communication protocols such as Infiniband, Ethernet, Gigabit Ethernet, SCSI, iSCSI, Fibre Channel, Fibre Channel over Ethernet, and the like. Such inter-node communication does not need the network that the user is attached to. Applications in the system management node 540 may interact with the parallel file system 518 by making system calls to an operating system kernel 543 that is coupled to the parallel file system interface 542. The system management node 540 may further include a user interface component 541 to allow a user to perform management tasks relating to the various nodes in the distributed system 500 via network 502.

The system management node 540 may include a set of management software targeted at the customer's administrative users who perform management functions, but are not allowed to see customer data. The management software may also be targeted at service personnel authorized by the customer for the collection of logs or other service data. The software may be accessed through a browser, a graphic user interface or a command line and available only on the system management node 540. A user or service user may need to directly login to any node, be locally defined on the system management node 540 and authorized to an administrative group as having authority to access system administration capabilities.

Administrative functions may include the ability to create/remove a file system, change the configuration of a file system by adding or deleting storage, and mount/unmount/export file system or other shares. The functions may further create/delete filesets, create/delete snapshots, create management users, manage attachment to the customer network including bonding and IP configuration after the initial configuration, and configure to use customer user directories. An embodiment may provide a GUI with administrative capabilities which are built upon those provided in a Scaled Out File System (SoFS) for monitoring the state of various components. The GUI may be accessed through a browser and provide user screens for management of storage, file system, pool, fileset, policy management, synchronous and asynchronous replication, hierarchical storage management, TSM management, snapshot, cluster, file access protocols, event log presentation, resource availability and utilization (CPU, memory, I/O), file system utilization (capacity), pool/disk utilization (capacity), notifications, call-home functions, and hardware monitoring.

In exemplary embodiments of the invention, the application nodes, storage nodes, interface nodes, system management node, and storage management server in the distributed systems 200, 400 and 500 may communicate with each other through their parallel file system interfaces and operating system kernels. A parallel file system interface may be a GPFS open source portability layer 307 as shown in FIG. 3. The GPFS open source portability layer 307 is a set of source files that can be compiled to provide a Linux kernel abstraction layer for GPFS and is used to enable communication between the Linux kernel and the GPFS kernel modules. The GPFS open source portability layer 307 may reside within the Linux kernel 306.

Embodiments of the invention may include a GPFS kernel module extension for providing interfaces to a virtual file system (VFS) for accessing a file system. The GPFS kernel module extension may be a kernel extension 308 shown in FIG. 3. Structurally, applications issue file system calls to the operating system, which in turn presents the calls to the GPFS file system kernel extension. The GPFS thus appears to applications as just another file system. The GPFS kernel extension will either satisfy these requests using resources that are already available in the system, or send a message to the daemon to complete the request. The GPFS kernel module extension 308 may reside within the Linux kernel 306.

The distributed system 500 may further comprise a GPFS daemon to perform all I/O and buffer management for GPFS, including read-ahead for sequential read and write-behind for all writes not specified as synchronous. The GPFS daemon may be GPFS daemon 302 as shown in FIG. 3. All I/O is protected by token management, which ensures data consistency of the systems. The GPFS daemon 302 is a multi-threaded process with some threads dedicated to specific functions. This ensures that services requiring priority attention are not blocked because other threads are busy with routine work. The GPFS daemon 302 also communicates with instances of the daemon on other nodes to coordinate configuration changes, recovery, and parallel updates of the same data structures.

The scalable and distributed systems illustrated in FIGS. 1-2 and 4-5 may be adapted to support the Digital Imaging and Communications in Medicine (DICOM) standard for handling, storing, printing, and transmitting information in medical imaging. DICOM includes a file format definition and a network communications protocol. The communication protocol is an application protocol that uses TCP/IP to communicate between systems. DICOM files can be exchanged between two entities that are capable of receiving image and patient data in DICOM format. DICOM enables the integration of scanners, servers, workstations, printers, and network hardware from multiple manufacturers into a picture archiving and communication system (PACS). The different devices come with DICOM conformance statements which clearly state the DICOM classes they support. DICOM has been widely adopted by hospitals and is making inroads in smaller applications like dentists' and doctors' offices. DICOM is known as NEMA standard PS3, and as ISO standard 12052. The use of the parallel file systems 218 (FIG. 2), 418 (FIG. 4), and 518 (FIG. 5), along with the cluster database 425-426 (FIG. 4) and 526 (FIG. 5) allow DICOM to be scaled beyond individual installations in separate doctor offices and hospitals into an worldwide integrated system, allowing the seamless communication among application nodes 203-204, 403-404 and 503-504, storage nodes 205, 405 and 505, and users 201, 401 and 501.

Figure 6:
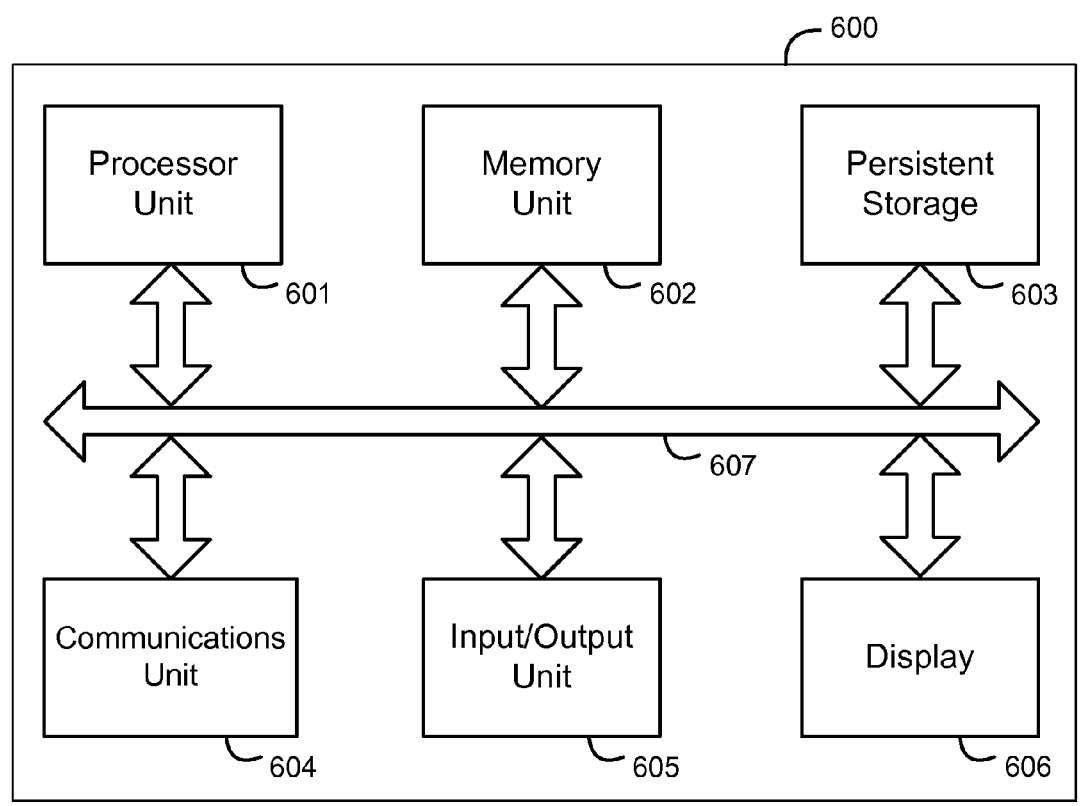
FIG. 6 illustrates a block diagram of a representative computer system that may be used in a distributed data sharing and storage system for providing aspects of the disclosure.

FIG. 6 illustrates a block diagram of a representative computer system that may be used in a distributed data sharing and storage system for providing aspects of the disclosure. Data processing system 600 may include a processor unit 601, a memory unit 602, a persistent storage 603, a communications unit 604, an input/output unit 605, a display 606 and a system bus 607. Computer programs are typically stored in persistent storage 603 until they are needed for execution by an operating system (not shown) running in memory unit 602. At that time, the programs are brought into the memory unit 602 so that they can be directly accessed by the processor unit 601. The processor unit 601 selects a part of memory unit 602 to read and/or write by using an address that the processor 601 gives to memory 602 along with a request to read and/or write. Usually, the reading and interpretation of an encoded instruction at an address causes the processor 601 to fetch a subsequent instruction, either at a subsequent address or some other address. The processor unit 601, memory unit 602, persistent storage 603, communications unit 604, input/output unit 605, and display 606 interface with each other through the system bus 607.

As will be appreciated by one skilled in the art, aspects of the present disclosure may be embodied as a method, system or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN), a wide area network (WAN), Ethernet, or the connection may be made to an external computer, for example, through the Internet using an Internet Service Provider.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures described above illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The subject matter described above is provided by way of illustration only and should not be construed as limiting. Various modifications and substitutions of the described components and operations can be made by those skilled in the art without departing from the spirit and scope of the present disclosure defined in the following claims, the scope of which is to be accorded the broadest interpretation so as to encompass such modifications and equivalent structures. As will be appreciated by those skilled in the art, the systems, methods, and procedures described herein can be embodied in a programmable computer, computer executable software, or digital circuitry. The software can be stored on computer readable media. For example, computer readable media can include a floppy disk, RAM, ROM, hard disk, removable media, flash memory, a "memory stick", optical media, magneto-optical media, CD-ROM, etc.

What is claimed is:

1. A distributed system, compromising:
a network;
a storage node coupled to the network for storing data;
a plurality of application nodes coupled to the network; and
a parallel file structure disposed across the storage node and application nodes to allow data storage, access and sharing through the parallel file structure,
wherein at least one of the application nodes comprises at least one medical modality selected from a group consisting of an echo-cardiogram modality, an electrocardiogram modality, an electromyography modality, an oncology modality, an angiography modality, and an electrophysiology modality;
one or more external tape libraries in communication with the distributed system;

one or more virtual tape libraries in communication with the distributed system;
one or more data de-duplication services in communication with the distributed system;
an interface node, comprising:
    a plurality of file access modules, and
    a clustered trivial database (CTDB) coupled to the file access modules and the parallel file structure;
    wherein the interface node is configured to:
        access the parallel file structure using file access protocols respectively supported by the modules; and
        provide high availability features including at least one of node monitoring, node fail-over and IP address takeover; and
    allow user and program access to the system;
a system management node; and
a storage management server, comprising:
    a device driver configured to communicate with an archival storage device; and
    a kernel configured to communicate with the device driver and the parallel file structure,
    wherein the device driver resides within the kernel, and
    wherein the storage management server is configured to:
        encapsulate data to be archived in an MXF wrapper; and
        back up and archive data to a tape library, and
wherein the storage node comprises multiple RAID disk arrays accessed via the device driver,
wherein the storage node is configured to access the parallel file structure through kernel system calls;
wherein at least one of the application nodes comprises:
    a local data storage;
    a driver configured to access the local data storage;
    a kernel configured to communicate with the driver and the parallel file structure; and
wherein the parallel file structure further comprises a plurality of reliable scalable cluster technology (RSCT) daemons configured to provide topology services and group services over the parallel file structure, and
wherein the parallel file structure is further disposed across the system management node and the storage management server
wherein the parallel file structure further comprises a plurality of reliable scalable cluster technology (RSCT) daemons configured to provide topology services and group services over the parallel file structure
wherein each RSCT daemon is further configured to:
    allocate disk space to one or more new files;
    allocate disk space to one or more newly extended files;
    search the parallel file structure;
    allocate one or more data locks to protect data integrity;
    allocate one of more metadata locks to protect metadata integrity;
    initiate one or more disk input/output (I/O) operations on one or more threads of the RSCT daemon;
    manage a parallel file structure security in conjunction with a file system manager; and
    manage one or more parallel file structure quotas in conjunction with the file system manager
wherein each daemon comprises a multi-threaded process, wherein at least one daemon comprises a dedicated thread.

2. A computer implemented method configured to share data in a distributed system comprising a storage node and a plurality of application nodes, the method comprising:

providing a parallel file structure across the storage node and application nodes to allow the application nodes to store data in the storage node through the parallel file structure; and
accessing data in the distributed system through the parallel file structure via a multi-threaded process comprising at least one dedicated threat;
wherein the distributed system further comprises:
one or more external tape libraries in communication with the distributed system;
one or more virtual tape libraries in communication with the distributed system;
one or more data de-duplication services in communication with the distributed system;
an interface node, comprising:
    a plurality of file access modules, and
    a clustered trivial database (CTDB) coupled to the file access modules and the parallel file structure;
    wherein the interface node is configured to:
        access the parallel file structure using file access protocols respectively supported by the modules; and
        provide high availability features including at least one of node monitoring, node fail-over and IP address takeover; and
    allow user and program access to the system;
a system management node; and
a storage management server, comprising:
    a device driver configured to communicate with an archival storage device; and
    a kernel configured to communicate with the device driver and the parallel file structure,
    wherein the device driver resides within the kernel, and
    wherein the storage management server is configured to:
        encapsulate data to be archived in an MXF wrapper; and
        hack up and archive data to a tape library, and
wherein the storage node comprises multiple RAID disk arrays accessed via the device driver,
wherein the storage node is configured to access the parallel file structure through kernel system calls;
wherein at least one of the application nodes comprises:
    a local data storage;
    a driver configured to access the local data storage;
    a kernel configured to communicate with the driver and the parallel file structure; and
wherein at least one of the application nodes comprises at least one medical modality selected from a group consisting of an echo-cardiogram modality, an electrocardiogram modality, an electromyography modality, an oncology modality, an angiography modality, and an electrophysiology modality;
wherein the parallel file structure further comprises a plurality of reliable scalable cluster technology (RSCT) daemons configured to provide topology services and group services over the parallel file structure, and
wherein the parallel file structure is further disposed across the system management node and the storage management server
wherein the parallel file structure further comprises a plurality of reliable scalable cluster technology (RSCT) daemons configured to provide topology services and group services over the parallel file structure
wherein each RSCT daemon is further configured to:
    allocate disk space to one or more new files;
    allocate disk space to one or more newly extended files;
    search the parallel file structure;
    allocate one or more data locks to protect data integrity;

allocate one or more metadata locks to protect metadata integrity;

initiate one or more disk input/output (I/O) operations on one or more threads of the RSCT daemon;

manage a parallel file structure security in conjunction with a file system manager; and manage one or more parallel file structure quotas in conjunction with the file system manager wherein each daemon comprises a multi-threaded process, wherein at least one daemon comprises a dedicated thread.

3. A computer program product configured to share data m a distributed system comprising a storage node and a plurality of application nodes, the computer program product comprising a non-transitory computer readable storage medium having computer readable program code embodied therewith, the computer readable program code comprising:

program code configured to provide a parallel file structure across the storage node and application nodes to allow the application nodes to store data in the storage node through the parallel file system; and program code configured to access the stored data through the parallel file system; and program code configured to provide hierarchical storage management (HSM) services to at least one of:

one or more external tape libraries in communication with the distributed system;

one or more virtual tape libraries in communication with the distributed system; and one or more data de-duplication services in communication with the distributed system;

wherein the distributed system further comprises:

one or more external tape libraries in communication with the distributed system;

one or more virtual tape libraries in communication with the distributed system;

one or more data de-duplication services in communication with the distributed system;

an interface node comprising:

a plurality of file access modules, and a clustered trivial database (CTDB) coupled to the file access modules and the parallel file structure;

wherein the interface node is configured to:

access the parallel file structure using file access protocols respectively supported by the modules; and provide high availability features including at least one of node monitoring, node fail-over and IP address takeover; and allow user and program access to the system;

a system management node; and a storage management server, comprising:

a device driver configured to communicate with an archival storage device; and a kernel configured to communicate with the device driver and the parallel file structure, wherein the device driver resides within the kernel, and wherein the storage management server is configured to:

encapsulate data to be archived in an MXF wrapper; and backup and archive data to a tape library, and wherein the storage node de comprises multiple RAID disk arrays accessed via the device driver, wherein the storage node is configured to access the parallel file structure through kernel system calls;

wherein at least one of the application nodes comprises:

a local data storage;

a driver configured to access the local data storage;

a kernel configured to communicate with the driver and the parallel file structure; and wherein at least one of the application nodes comprises at least one medical modality selected from a group consisting of an echo-cardiogram modality, an electrocardiogram modality, an electromyography modality, an oncology modality, an angiography modality, and an electrophysiology modality;

wherein the parallel file structure further comprises a plurality of reliable scalable cluster technology (RSCT) daemons configure to provide topology services and group services over the parallel file structure, and wherein the parallel file structure is further disposed across the system management node and the storage management server wherein the parallel file structure further comprises a plurality of reliable scalable cluster technology (RSCT) daemons configure to provide topology services and group services over the parallel file structure, and wherein each of the RSCT daemon is further configured to:

allocate disk space to one or more new files;

allocate disk space to one or more newly extended files;

search the parallel file structure;

allocate one or more data locks to protect data integrity;

allocate one or more meta data locks to protect meta data integrity;

initiate one or more disk input/output (I/O) operations on one or more threads of the RSSCT daemon;

manage a parallel file structure security in conjunction with a file system manager; and manage one or more parallel file structure quotas in conjunction with the file system manager wherein each daemon comprises a multi-threaded process, wherein at least one daemon comprises a dedicated thread.

\* \* \* \* \*